(12) United States Patent
Kang

(10) Patent No.: US 8,666,487 B2
(45) Date of Patent: Mar. 4, 2014

(54) DEVICE FOR SKIN TREATMENT

(76) Inventor: Dong Hwan Kang, Gwangmyeong-si (KR)

(*) Notice: Subject to any disclaimer, the term of this patent is extended or adjusted under 35 U.S.C. 154(b) by 235 days.

(21) Appl. No.: 12/922,087

(22) PCT Filed: Jan. 13, 2010

(86) PCT No.: PCT/KR2010/000200
§ 371 (c)(1),
(2), (4) Date: Dec. 15, 2010

(87) PCT Pub. No.: WO2010/085059
PCT Pub. Date: Jul. 29, 2010

(65) Prior Publication Data
US 2011/0092884 A1 Apr. 21, 2011

(30) Foreign Application Priority Data

Jan. 23, 2009 (KR) .................. 10-2009-0006081
Jul. 2, 2009 (KR) .................. 10-2009-0060237

(51) Int. Cl.
*A61N 1/30* (2006.01)
(52) U.S. Cl.
USPC .................................. 604/21; 604/173
(58) Field of Classification Search
USPC ......... 604/19, 20, 21, 117, 173; 607/116, 148
See application file for complete search history.

(56) References Cited

U.S. PATENT DOCUMENTS

| | | | |
|---|---|---|---|
| 3,035,580 A * | 5/1962 | Guiorguiev | 606/44 |
| 4,679,551 A * | 7/1987 | Anthony | 601/160 |
| 6,009,347 A | 12/1999 | Hofmann | |
| 6,120,493 A | 9/2000 | Hofmann | |
| 6,233,482 B1 | 5/2001 | Hofmann et al. | |
| 6,277,116 B1 | 8/2001 | Utely et al. | |
| 6,549,797 B1 | 4/2003 | Leonard et al. | |
| 6,556,869 B1 | 4/2003 | Leonard et al. | |

(Continued)

FOREIGN PATENT DOCUMENTS

| JP | 2005-528935 A | 9/2005 |
|---|---|---|
| JP | 2007-531578 A | 11/2007 |

(Continued)

OTHER PUBLICATIONS

Written Opinion of the ISA/KR issued in parent PCT application No. PCT/KR2010/000200 on Sep. 8, 2010, with English-language translation of the annexes, 5 pages.

*Primary Examiner* — Kami A Bosworth
(74) *Attorney, Agent, or Firm* — Drinker Biddle & Reath LLP

(57) ABSTRACT

A device for skin treatment, which precisely transmits high-frequency energy to a target portion of skin tissue without causing a burn on the outer layer of the skin, thus artificially damaging the portion and inducing a wound curing reaction, therefore leading to the regeneration of skin and the propagation of collagen. The device prevents the surface of skin from suffering an injury during insertion, alleviates pain, and keeps the depth to which the needle is inserted into the skin uniform. The device includes a plurality of needles coated with an insulator except for sharp ends. A needle holding unit holds the needles. A drive unit directly or indirectly transmits a force to the needle holding unit, thus allowing the needles to be inserted into the skin. An electromagnetic wave transmitting unit is electrically connected to the needles and transmits electromagnetic waves to the needles.

32 Claims, 19 Drawing Sheets

(56) References Cited

U.S. PATENT DOCUMENTS

| | | |
|---|---|---|
| 6,678,558 B1 | 1/2004 | Dimmer et al. |
| 6,713,291 B2 | 3/2004 | King et al. |
| 7,054,685 B2 | 5/2006 | Dimmer et al. |
| 7,278,991 B2 | 10/2007 | Morris et al. |
| 7,331,953 B2 | 2/2008 | Manstein et al. |
| 2002/0061589 A1 | 5/2002 | King et al. |
| 2004/0203124 A1 | 10/2004 | King et al. |
| 2005/0137662 A1 | 6/2005 | Morris et al. |
| 2006/0224192 A1 | 10/2006 | Dimmer et al. |
| 2009/0076497 A1 | 3/2009 | Morris et al. |
| 2009/0259180 A1 * | 10/2009 | Choi .............................. 604/117 |

FOREIGN PATENT DOCUMENTS

| | | |
|---|---|---|
| KR | 10-2006-0016868 A | 2/2006 |
| WO | 03/079916 A1 | 10/2003 |
| WO | 2005/096979 A1 | 10/2005 |

* cited by examiner

DEVICE FOR SKIN TREATMENT

CROSS-REFERENCE TO RELATED APPLICATIONS

This application is the U.S. national phase of International Patent Application No. PCT/KR2010/00200 filed Jan. 13, 2010, which claims the benefit of Korean Application No. 10-2009-0006081 filed Jan. 23, 2009, both of which are incorporated herein by reference. This application also claims the priority of Korean Patent Application No. 10-2009-0060237, filed Jul. 2, 2009 in the Korean Patent Office, which is incorporated herein by reference in its entirety.

BACKGROUND

1. Field of the Invention

The invention relates generally to a device for skin treatment and, more particularly, to a device for skin treatment, which is constructed such that a plurality of needles coated with an insulator is inserted into the skin and an electromagnetic wave is transmitted through the needles inserted into the skin.

2. Description of the Related Art

As seen in paper 1 (Hyun-Ju Jeong, The measurement of the thickness of the Korean's skin by ultrasound, KyungBuk Univ., 1990. Vol. 28(2), 121-129) and paper 2 (Jin-Sung Park, The measurement of the thickness of the Koreans' skin by a CT scan, Catholic Univ., 1995. Vol. 33, 303-311), the thickness of an Oriental's skin is generally about 1.5 mm to 4.0 mm, and the thickness of the outer layer of the skin is about 0.06 mm to 0.2 mm.

For example, in terms of the thickness of the skin, the cheek which has the thickest skin is about 2.7 mm (±0.40 mm), and the forehead and the eyelid which have the thinnest skin are about 0.84 mm.

A person's skin consists of an outer layer and an inner layer. The inner layer serves as the main support of the skin and is made up of a protein which is called collagen. The collagen has a triple helical structure including a fibroblst and a polypeptide. If the collagen tissue is heated, the protein matrix is physically changed at the shrinkage temperature. The remodeling of soft tissue is a physical change that occurs at the cellular or molecular level. The shrinkage or the partial denaturization of collagen generated by artificial heat decomposes the bonding of a triple helix, thus destroying the intermolecular bonding of the matrix. When it is compared with the shrinkage resulting from the movement of fibroblasts into a wound and natural healing power, the remodeling of soft tissue is an immediate process. When cells shrink, the collagen is situated at a lower position and acts as a static support matrix for the taut soft tissue. The initial deposition of a scar matrix and the subsequent remodeling provide means for changing the shape and consistency of soft tissue for beauty purposes.

Generally, in order to treat various scars or skin lesions or to improve the skin or wrinkles for the sake of beauty, a method of applying various energy sources to an associated portion and solidifying the tissue has been used. For example, methods of transferring thermal energy have been proposed.

According to the methods, various kinds of energy are applied to the target portions of the skin tissue to intentionally cause wounds, thus stimulating the collagen of the inner layer and inducing the regenerating action of the collagen, therefore regenerating skin tissue.

Referring to papers, it is reported that the denaturization of collagen occurs most reliably at a temperature from 65° C. to 75° C. However, the effects of treatment may vary according to how the patient endures the pain at this temperature.

Conventionally, a target portion of the skin is heated by radiating light, near infrared rays, and microwaves. According to the conventional methods, heat is applied to the outer layer of the skin to reach the target portion of the skin.

However, when thermal energy is transmitted from the outer portion of the skin to the target portion (the outer layer, inner layer, or subcutaneous fat) of skin tissue, the thermal energy is greatly scattered or absorbed. Thus, there is less energy to be substantially transmitted to the inner layer. If the thermal energy which is applied to the skin is increased to solve the problem, the outer layer is burned.

Further, a method of using physical energy has been proposed. According to the method, a superfine needle is inserted into a target portion of the skin tissue to physically stimulate it. However, the method is problematic in that a user personally inserts the needle into the skin, so that it is difficult to precisely control the depth to which the needle is inserted into the target portion of skin tissue. When this method is used, the skin is damaged only physically and not damaged thermally, so that the effect of regenerating collagen or damaged skin is restricted. Further, if the needle is inserted at an angle to the outer layer of the skin, an incident angle differs from an emergent angle, so that a wound may undesirably result and the inner layer of the skin may be stimulated.

Further, when a roller equipped with a plurality of needles is rubbed against the skin, an incident angle differs from an emergent angle, thus causing an undesirable wound and pain.

Further, the important parameters of a conductive needle which transmits electromagnetic waves to the skin include the angle of the conductive needle when it is inserted into the skin and the diameter of the conductive needle. Since pain and a burn are caused when the conductive needle is inserted into the skin, there is a need for the development of a conductive needle which is optimized to eliminate the pain and burning. However, the conventional conductive needle is manufactured indiscriminately without taking into consideration the angle and diameter of the conductive needle. Therefore, it is difficult to eliminate the pain and burning.

A conventional device having a needle unit is problematic in that needles to which high-frequency waves are applied are inserted directly by a user using his or her hand, so that the depth of insertion, the strength, a balanced state during insertion, and the time it takes to perform the insertion are not constant. Consequently, the conventional device varies in treatment effect, pain, and operation time, so that it is difficult to standardize the treatment effect, pain, and operation time.

In order to accomplish the purpose of a desired treatment, a plurality of needles must be almost simultaneously inserted into the body, and electric energy must be applied to ends of the needles. When the plurality of needles is inserted into a very shallow layer of the skin, the depth of the end of each needle must be precisely controlled according to a predetermined value.

When the plurality of needles is not controlled horizontally as shown in FIG. 1, the surface of the skin may be undesirably damaged. Therefore, a method of controlling the plurality of needles horizontally is required.

Further, in the case of inserting the device into the human body, it must always be inserted into the skin using regular pressure so as to lessen the sensation of fear and pain of a patient.

FIG. 2 is a graph illustrating survey results regarding the fear and pain felt when medical treatment is performed on people receiving clinical treatment using irregular pressure.

The graph shows that people receiving clinical treatment suffer more fear and pain under irregular pressure in comparison with regular pressure.

The needles inserted into the skin must always be dislodged from the skin within a predetermined period of time so as to remove the danger of an accident and lessen the pain.

If the needles are dislodged from the skin at a different time for each shot during the medical treatment, the skin may be scratched by the needles or high-frequency waves may be directly applied to the outer layer of the skin while one portion of the skin has been treated and then the needles are moved, so that the skin may be undesirably damaged as shown in FIG. 3. Further, if the needles stay in the skin for a lengthy period of time, a patient's pain increases.

FIG. 4 is a graph showing survey results for people receiving clinical treatment. As shown in the drawing, as time for inserting the needles into the skin increases, the number of people receiving clinical treatment who feel pain increases.

The conventional device is problematic in that it is impossible to know the replacement time even if the needles are no longer being used.

As shown in FIGS. 5 to 7, when a predetermined period of time has passed or the needles have been used for a predetermined number times, the ends of the needles are undesirably burnt or bent. Thus, when a predetermined period of time has passed or the needles have been used for a predetermined number times, it is necessary to prevent the use of the needles for safety's sake. Further, in the case of simultaneously using a bipolar type needle and a monopolar type needle, a user must control the amount of energy or know whether opposite pole plates are installed or not. Thus, means for storing and displaying these pieces of information is required.

The method and object of treatment depend on the using amount or characteristics of the needles. Thus, a sensing device is required to read pieces of information of the needles and control the parameters of the equipment.

If the needles are inserted into the skin to a depth of 0.2 mm or more and high-frequency energy is applied, a very small amount of protein denaturation occurs. The denatured protein sticks to the needles, so that the needles are not easily removed from the skin.

If the needles slide horizontally with not being removed from the skin, the skin is damaged by the needles as shown in FIG. 3.

Further, when the plurality of needles is inserted into the skin, the longer the time taken to insert the needles into the skin is, the greater a patient's fear and pain are. Thus, it is required to reduce the time taken to insert as much as possible. Further, when the needles are inserted using the hand, fine vibrations are generated rightward and leftward. A treatment which is not standardized increases the patient's fear and pain. FIG. 8 is a diagram showing patients' pain as a function of the speed and method used to insert the needles.

A pushing force of an electric-powered device such as a solenoid valve is weaker than a recovery force, so that a means for supplementing the recovery force and aiding in removing the needles from the skin is required. Therefore, it is required to reduce the time it takes to separate the needles from the skin for safety's sake, thus reducing the stress of an operator and a patient.

SUMMARY

Accordingly, the invention has been made keeping in mind the above problems occurring in the prior art, and an embodiment of the invention provides a device for skin treatment, in which a needle passes through an outer skin layer to be inserted into an inner skin layer or the desired skin tissue and applies high-frequency energy thereto, thus allowing the skin to be treated without causing a burn.

An embodiment of the invention provides a device for skin treatment, which is capable of precisely transmitting energy to a desired portion of skin tissue.

An embodiment of the invention provides a device for skin treatment, which optimizes the shape of a needle so that incident and emergent angles of the needle relative to the skin are equal to each other, and the insertion speed and the recovery speed are standardized and increased, thus lessening an operator's stress and alleviating a patient's pain.

An embodiment of the invention provides a device for skin treatment, which automatically controls the kind, life span, and other pieces of information about a needle that is an article of consumption, thus enhancing reliability.

In order to accomplish the above objects, an embodiment of the invention provides a device for skin treatment including a plurality of needles, portion of each of the needles except for a sharp end being coated with an insulator, a needle holding unit for holding the needles, a drive unit for directly or indirectly transmitting a force to the needle holding unit, thus allowing the needles held by the needle holding unit to be inserted into the skin, and an electromagnetic wave transmitting unit electrically connected to the needles and transmitting electromagnetic waves to the needles.

As is apparent from the above description, such a device for skin treatment is advantageous in that a burn produced on the surface of the skin during the insertion of a conductive needle is eliminated and the pain is alleviated, and the insertion of the conductive needle into the skin is uniformly carried out, thus allowing the skin to be more efficiently treated as electromagnetic waves are applied. Further, safer treatments are possible because information about a needle is controlled using memory.

BRIEF DESCRIPTION OF THE DRAWINGS

The above and other objects, features and advantages will be more clearly understood from the following detailed description of various embodiments taken in conjunction with the accompanying drawings, in which.

DESCRIPTION OF THE PREFERRED EMBODIMENTS

Hereinafter, the construction and operation of embodiments of the invention will be described with reference to the accompanying drawings.

Figure 1:
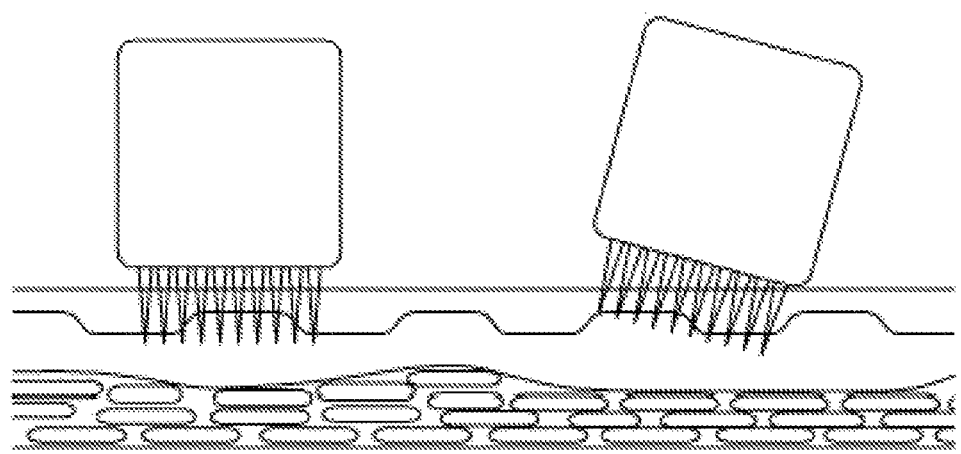
FIGS. 1 to 8 are views illustrating the problems of a conventional device for skin treatment.
Figure 2:
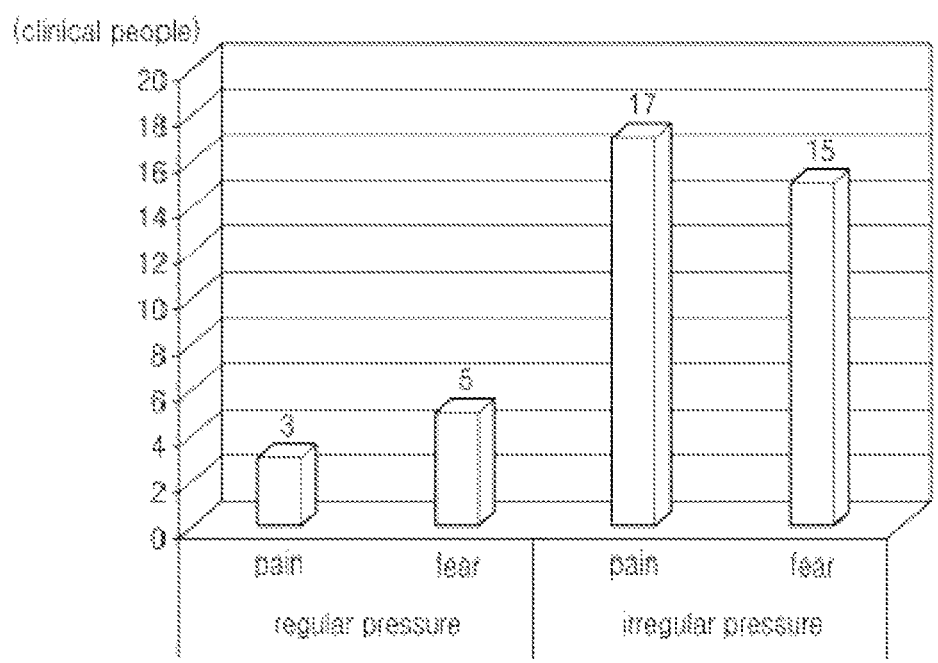
Figure 3:
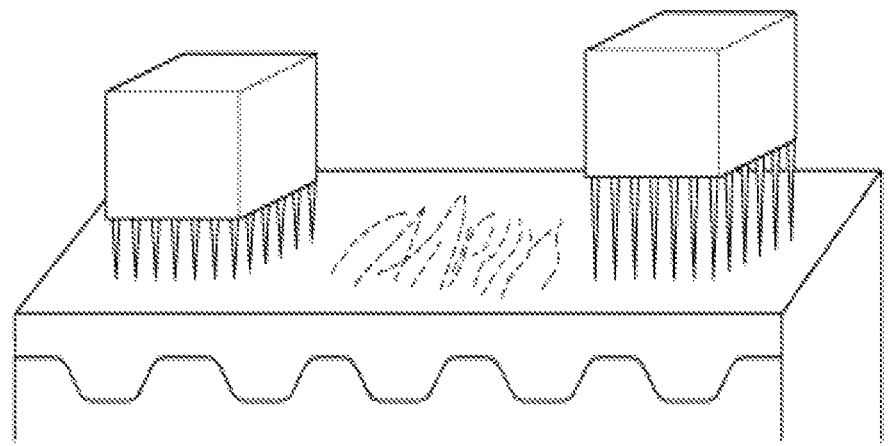
Figure 4:
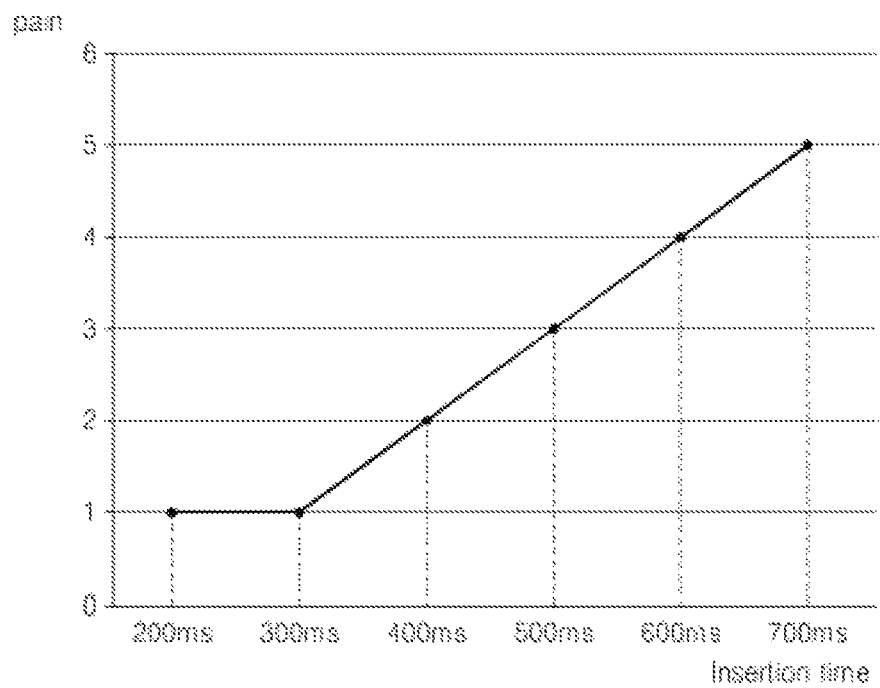
Figure 5:
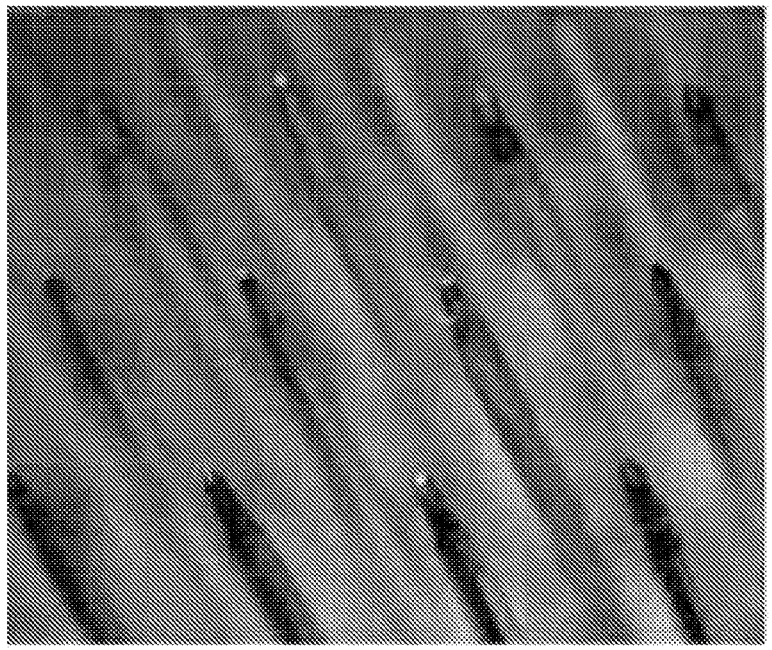
Figure 6:
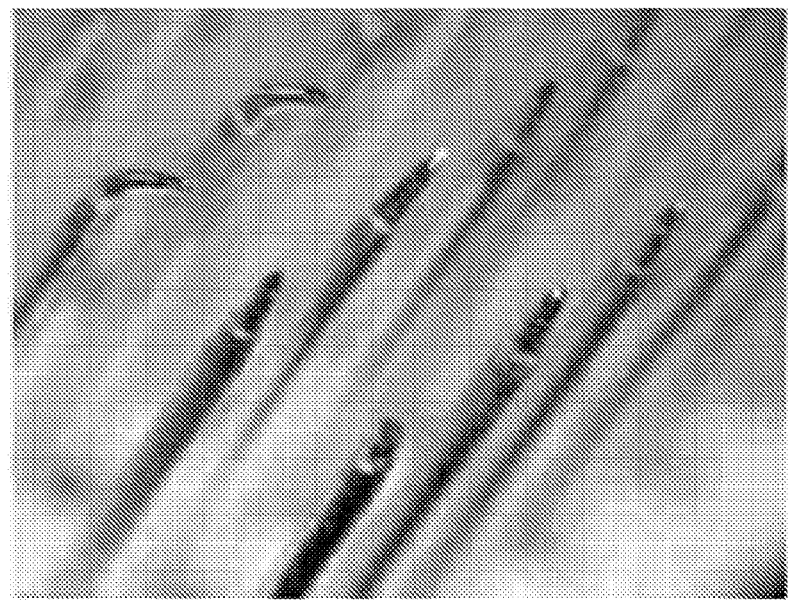
Figure 7:
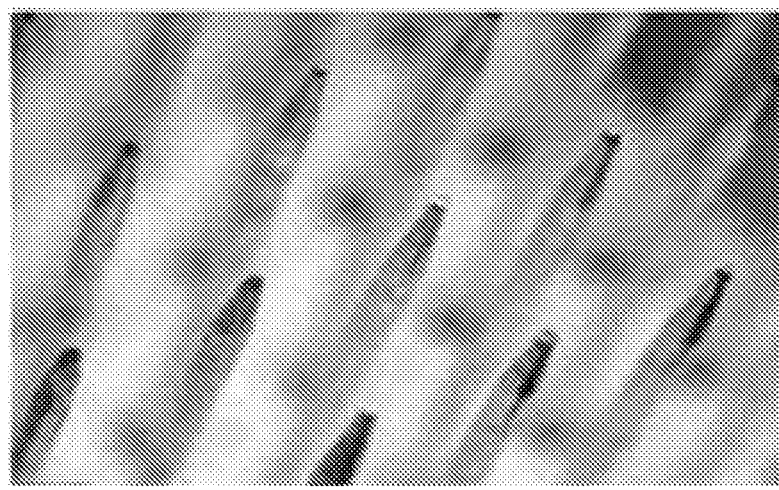
Figure 8:
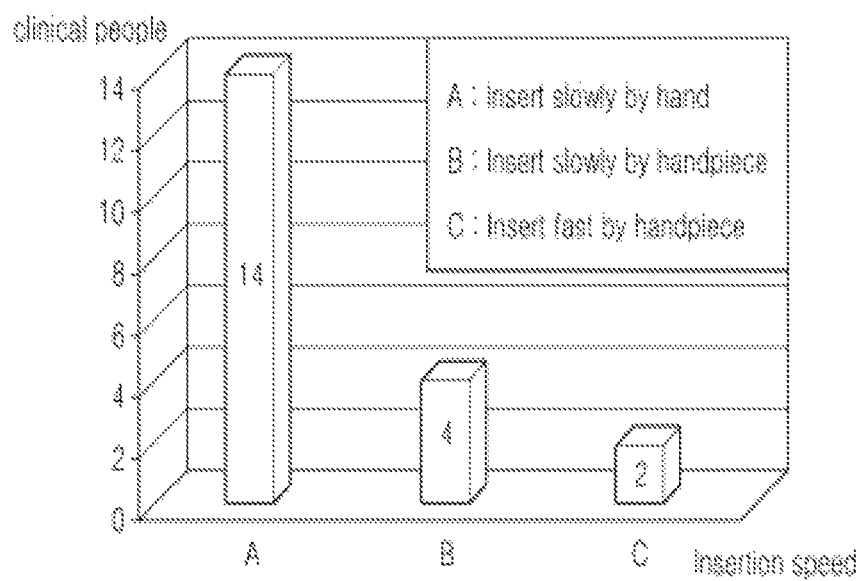
Figure 9:
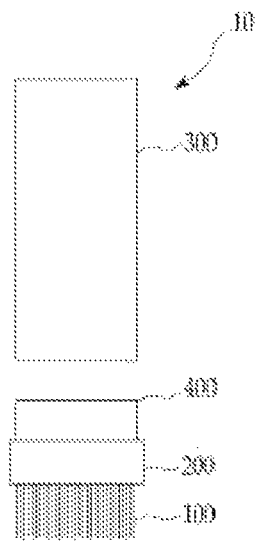
FIG. 9 is a view illustrating the construction of a device for skin treatment according to an embodiment of the invention.

FIG. 9 is a view illustrating the construction of a device for skin treatment according to an embodiment of the invention. The skin treating device 10 includes a plurality of needles 100, a needle holding unit 200, a drive unit 300, and an electromagnetic wave transmitting unit 400. The needle holding unit 200 functions to hold the needles 100. The drive unit 300 directly or indirectly transmits a force to the needle holding unit 200 so that the needles 100 held by the needle holding unit 200 are inserted into the skin. The electromagnetic wave transmitting unit 400 is electrically connected to the needles 200 to transmit electromagnetic waves to the needles 100.

As soon as the needles 100 are inserted into the skin, they are held by the needle holding unit 200. One end of each needle 100 has a diameter of from 0.1 mm to 0.4 mm, while the other end is sharp. If one end of the needle 100 has a diameter less than 0.1 mm, the needle 100 may be easily bent and thus tear the skin when inserted into the skin. Meanwhile, if one end of the needle 100 has a diameter greater than 0.4 mm, pain and a burn may result when the needle 100 is inserted into the skin.

Preferably, the needle 100 is bent in one or more stages such that its angle changes between one end and the other end of the needle 100. Meanwhile, the needle 100 may be rounded without being bent between one end and the other sharp end. Such a shape serves to alleviate the pain caused when the needle 100 is inserted into the skin.

Further, portion of each needle 100 except for the sharp end is preferably coated with any one of Parylene, Teflon, and ceramic to a thickness of from 5 μm to 25 μm. Such a coating enables electromagnetic waves transmitted through the needles 100 to the skin to be emitted to a desired depth in the skin. The coating layer preferably has a thickness of from 5 μm to 25 μm so as to maintain the advantages of the Parylene coating and to prevent impurities from remaining after the coating operation. Parylene coating is thermally excellent because its properties, such as thermal or mechanical deformation, do not change within a range from −200° C. to 150° C. Parylene coating enables a coating layer to be uniformly formed on the surface of the needle 100, in addition to permitting the adjustment of the thickness of the coating layer. Parylene coating is harmless to humans. The ceramic coating may use $Al_2O_3$, $ZrO_2$, glass ceramics, carbon, etc. The needle 100 may be made of stainless steel, for example, SUS303.

In order to emit electromagnetic waves to a desired depth of skin, each needle 100 is preferably shaped such that a first straight line connecting a first point which is in contact with the skin when the needle 100 is inserted into the skin with a sharp point of the needle end forms an angle of from 14° to 30° with a second straight line connecting a second point which faces the first point with the sharp point of the needle end.

Figure 10:
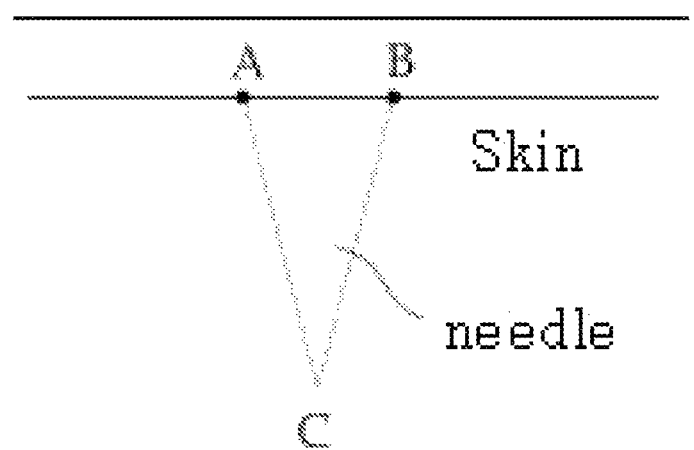
FIG. 10 is a view illustrating a needle inserted into the skin, according to an embodiment of the invention.

That is, assuming that the sharp point of the needle 100 is denoted by C, the first point is denoted by A, and the second point is denoted by B, and the first straight line connecting C with A forms an angle of from 14° to 30° with the second straight line connecting C with B, as shown in FIG. 10, electromagnetic waves are transmitted to the skin without inducing pain. When the angle between the first straight line and the second straight line is less than 14°, the end of the needle 100 becomes excessively thin, so that the needle 100 may be easily bent. Meanwhile, when the angle between the first and second straight lines is greater than 30°, the end of the needle 100 becomes dull, so that the needle 100 is not smoothly inserted into the skin and pain increases.

The needles 100 will be described in more detail with reference to the embodiments of FIGS. 11A to 11D.

A portion of each needle 100 from its sharp end to a first point, bent to be inclined relative to the sharp end at the angle of from 14° to 30°, is non-insulated. A portion of the needle 100 from the first point to a second point, bent to be inclined relative to the first point at the angle of from 2.5° to 12.5°, is coated with an insulator. A portion of the needle 100 from the second point to an end facing the sharp end is coated with an insulator while maintaining the diameter of 0.25 mm without being bent, so that electromagnetic waves are transmitted to the skin at the non-insulated portion.

To describe in detail, the needle 100 has a circular cross-section and is shaped such that its diameter is reduced from one end to the other end. Further, the needle 100 is bent in two stages and is sharp at the other end. The entire length of the needle 100 is preferably about 1.5 cm.

The needle 100 includes a first insulating portion 110, a second insulating portion 120, and a non-insulating portion 130, which are integrated with each other. The first insulating portion 110 has a diameter of 0.25 mm±0.05 mm, and is secured to the needle holding unit 200 which holds the needle 100 to allow it to be easily inserted into the skin.

The needles 100 may be formed as shown in the embodiments of FIGS. 11A to 11D.

Figure 11:
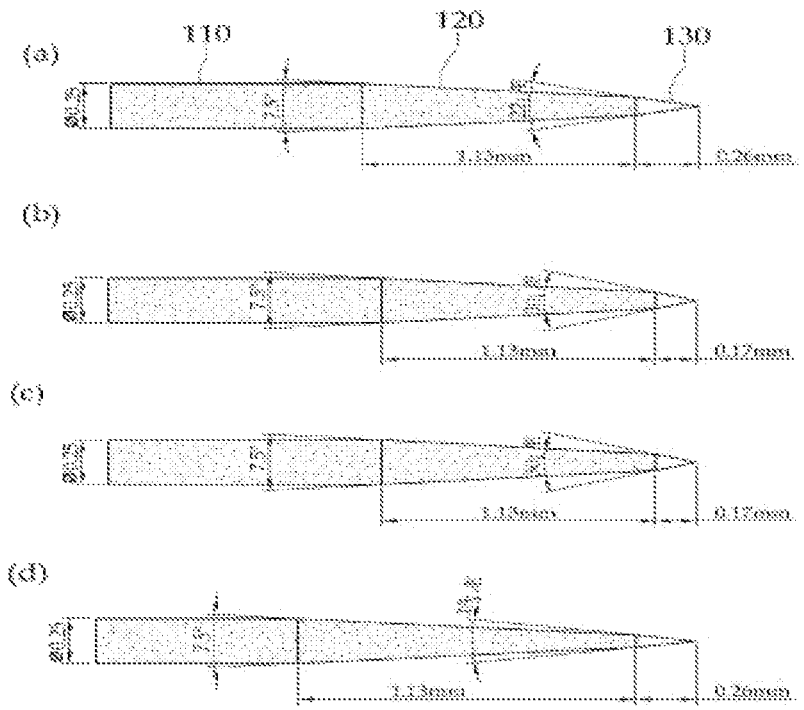
FIGS. 11A to 11D are views respectively illustrating a plurality of needles according to an embodiment of the invention.

That is, as shown in FIG. 11A, a needle is formed such that a portion extending from a sharp end to a first point, bent to be inclined relative to the sharp end at an angle of 22°, and having the length of about 0.26 mm±0.02 mm is non-insulated. Further, a portion of the needle extending from the first point to a second point, bent to be inclined relative to the first point at an angle of 7.5°, and having the length of about 1.13 mm±0.02 mm is coated with an insulator to a thickness of 10 μm±2 μm. A portion of the needle extending from the second point to an end facing the sharp end is coated with an insulator to a thickness of 10 μm±2 μm while maintaining the diameter of 0.25 mm without being bent. Electromagnetic waves are transmitted to the skin through the needle.

Next, as shown in FIG. 11B, a needle is formed such that a portion extending from a sharp end to a third point, bent to be inclined relative to the sharp end at an angle of 30°, and having the length of about 0.17 mm±0.02 mm is non-insulated. Further, a portion of the needle extending from the third point to a fourth point, bent to be inclined relative to the first point at an angle of 7.5°, and having the length of about 1.13 mm±0.02 mm is coated with an insulator to a thickness of 10 μm±2 μm. A portion of the needle extending from the fourth point to an end facing the sharp end is coated with an insulator to a thickness of 10 μm±2 μm while maintaining the diameter of 0.25 mm without being bent. Electromagnetic waves are transmitted to the skin through the needle.

A needle of FIG. 11C has the same structure as that of FIG. 11B, but is different from that of FIG. 11B because the coating thickness of the insulator is 20 μm±2 μm. The coating layer of FIG. 11C is thicker than that of FIG. 11B, thus preventing heat generated from the needle when electromagnetic waves are radiated from being transmitted to outside of the coating layer.

Further, as shown in FIG. 11D, a needle is formed such that a portion extending from a sharp end to a fifth point, bent to be inclined relative to the sharp end at an angle of 15°, and having the length of about 0.26 mm±0.02 mm is non-insulated. Further, a portion of the needle extending from the fifth point to a sixth point, bent to be inclined relative to the fifth point at an angle of 7.5°, and having the length of about 1.13 mm±0.02 mm is coated with an insulator to a thickness of 15 μm±10 μm. A portion of the needle extending from the fifth point to an end facing the sharp end is coated with an insulator to a thickness of 15 μm±10 μm while maintaining the diameter of 0.25 mm without being bent. Electromagnetic waves are transmitted to the skin through the needle.

The electromagnetic waves preferably range from 10 KHz to 100 MHz. A material of the needle 100 is stainless steel, and the thermal conductivity of the stainless steel is 14 cal/° C. Further, the needle 100 may be made of a general aluminum material.

Figure 12:
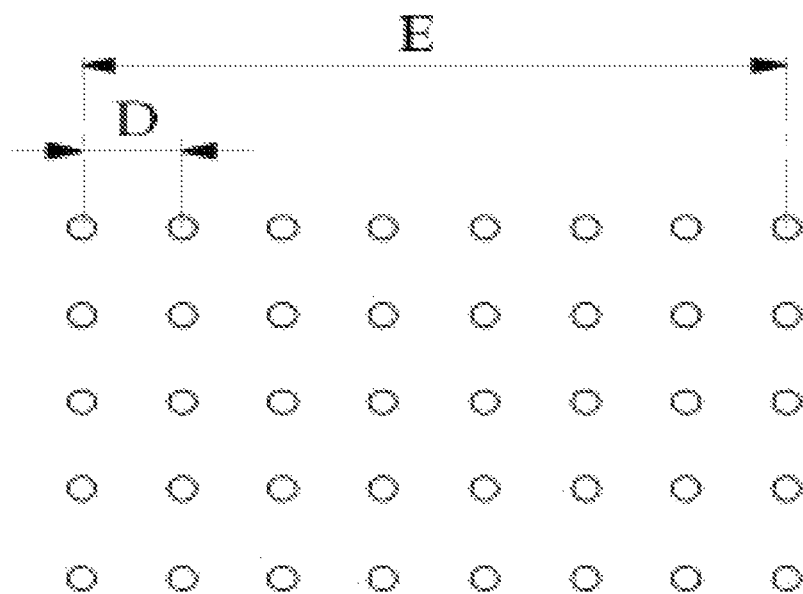
FIG. 12 is a view illustrating the arrangement of a plurality of needles according to an embodiment of the invention.

Preferably, 4 to 81 needles 100 are held by the needle holding unit 200 to form a group, and are inserted into the skin. That is, a proper number of needles 100 is selected according to the area of a portion which is to be treated, thus applying high-frequency waves to only the target portion. Especially, as shown in FIG. 12, an interval (D of FIG. 12) between neighboring needles preferably ranges from 0.4 mm to 3.0 mm. When the needles 100 are used to pull skin tissue and thereby reduce the area and volume of the skin tissue, the needles 100 are secured so as to form an interval of from 1.0 mm to 3.0 mm. Meanwhile, when the needles 100 are used to denature an entire portion like a scar, the interval between the needles 100 preferably ranges from 0.4 mm to 1.0 mm.

Further, it is preferable that a depth of the needles 100 inserted into the skin range from 0.3 m to 2.5 cm. The thickness of the skin except for a subcutaneous fat layer varies according to the region. The thickest portion of the skin is about 4 mm. In the case of improving the skin or scar, it is preferable that the depth of insertion of the needle range from 0.3 mm to 2 mm. In the case of treating the abdominal fat or the subcutaneous fat of a region of fat, it is preferable that the insertion depth of the needle range from 2 mm to 2.5 cm.

Moreover, the plurality of needles 100 is preferably arranged such that a distance (E of FIG. 12) between the first needle to the last needle ranges from 2 mm to 20 mm. If the distance E exceeds 20 mm, it is difficult for the skin to be completely in contact with the needles 100, and it is difficult to treat the skin under regular pressure, so that the skin may be scratched. If the distance E is less than 2 mm, the area treated is very small, so that the efficiency of treatment is low.

Figure 13:
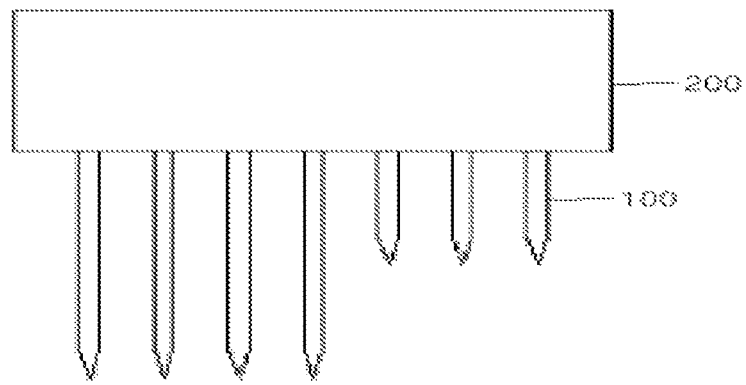
FIGS. 13 to 15 are views illustrating the arrangement of needles according to an embodiment of the invention.
Figure 14:
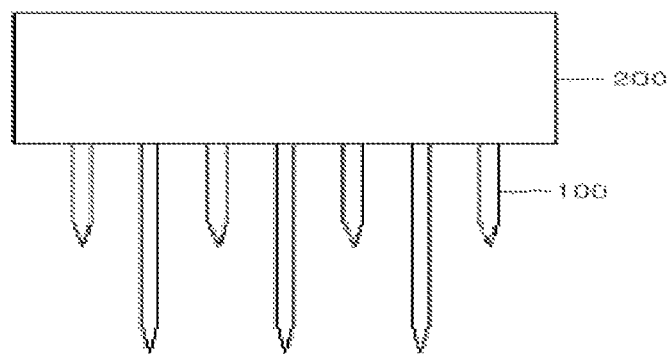
Figure 15:
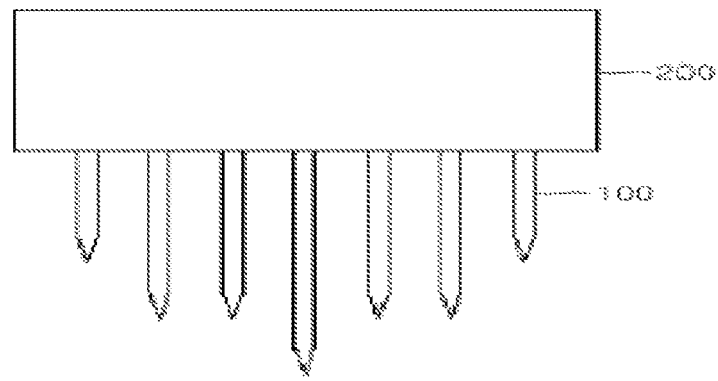

As shown in FIGS. 13 to 15, the needles 100 held by the needle holding unit 200 may comprise two or more kinds having different lengths.

Figure 16:
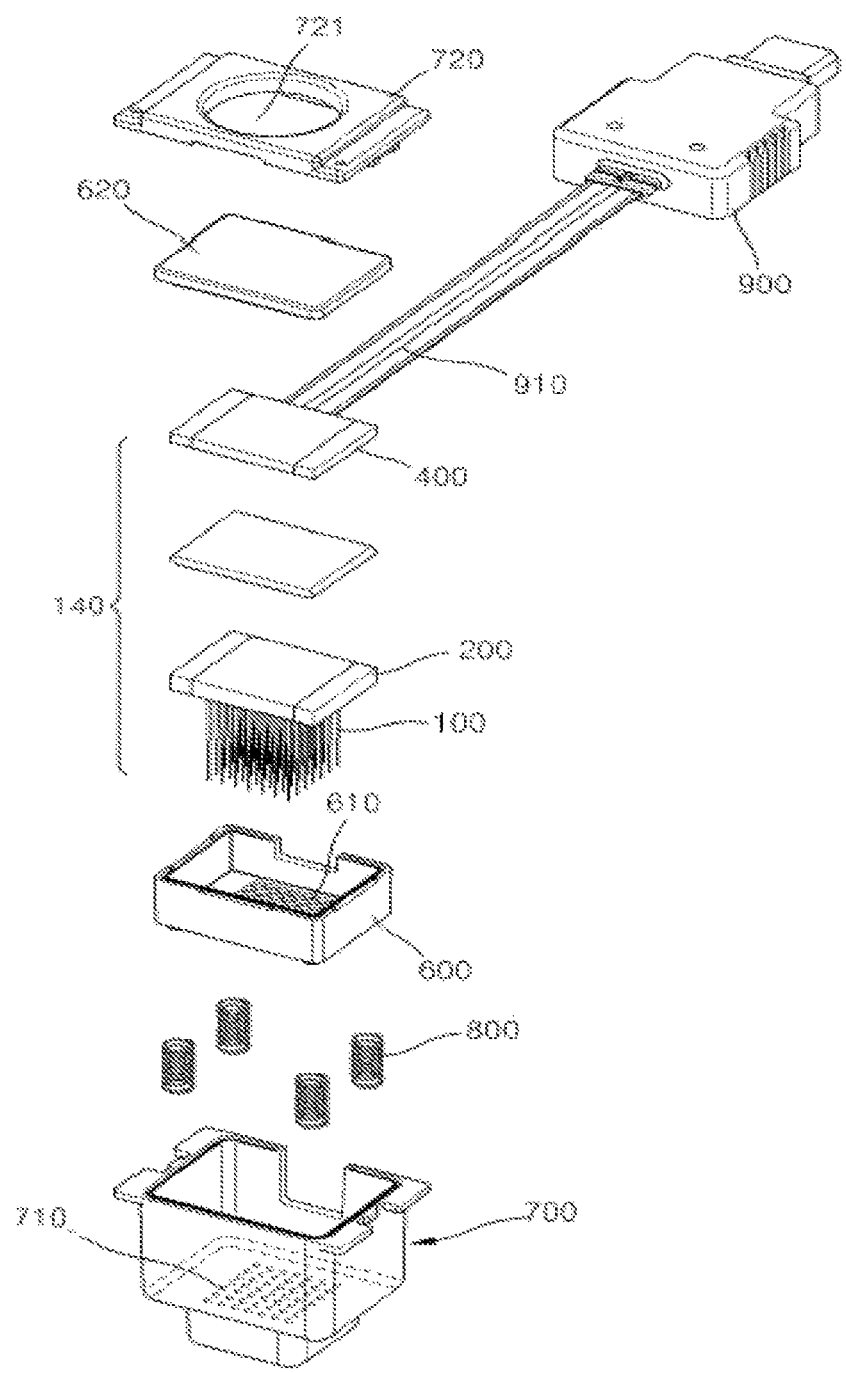
FIG. 16 is a view illustrating the assembly of a plurality of needles according to an embodiment of the invention.
Figure 17:
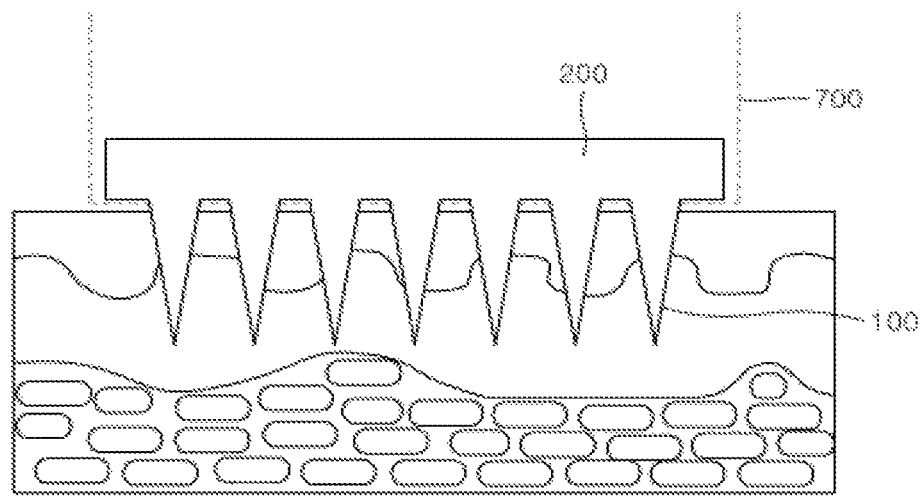
FIG. 17 is a view illustrating the function of a skin support member according to an embodiment of the invention.

For easy replacement when the needles 100 held by the needle holding unit 200 can no longer be used, the plurality of needles 100, the needle holding unit 200, and the electromagnetic wave transmitting unit 400 are preferably formed into one assembly 140. Referring to FIG. 16, an internal casing 600 is further provided, so that the needles 100, the needle holding unit 200, and the electromagnetic wave transmitting unit 400 are fitted into the open upper portion of the internal casing 600 to be protected. The internal casing 600 has in its lower portion a plurality of first holes 610 through which the needles 100 pass.

The device also includes a skin support member 700. The skin support member 700 has, on its lower portion which is in contact with the skin, second holes 710 to permit the passage of the needles 100, and is open at its upper portion. The assembly 140 having the needles 100, the needle holding unit 200, the electromagnetic wave transmitting unit 400 and the internal casing 600 is accommodated in the skin support member 700 through its open upper portion in such a way that the needles 100 pass through the second holes 710. If necessary, the needle holding unit 200 may be combined with the skin support member 700 without the internal casing 600.

The skin support member 700 functions to prevent the needle holding unit 200 holding the needles 100 from directly striking the skin. If the needle holding unit 200 should directly strike the skin, pain is caused when the needle holding unit 200 comes into contact with the skin. Thus, the skin support member 700 is positioned between the needle holding unit 200 and the skin, thus preventing the operating friction of the needle holding unit 200 from being directly transmitted to the skin. The skin support member 700 is preferably made of stainless steel having the thermal conductivity of 14 cal/° C.

The skin support member 700 allows the assembly 140 to be smoothly replaced by another one. Further, one or more elastic members 800 are provided on the surface of the skin support member 700 having the second holes 710, that is, the inner surface of the skin support member 700 which is not in contact with the skin, thus allowing the needles 100 to be immediately removed from the skin by the restoring force of the elastic members 800. Of course, the elastic members 800 may be provided between the needle holding unit 200 and the first holes 610.

Each elastic member 800 preferably comprises a spring. The elastic member 800 preferably has elastic restoring force such that the needles 100 inserted into the skin by being struck are removed from the skin within 2 seconds using elastic force. If the needles 100 are removed from the skin within 2 seconds, the surface of the skin is not scratched and the operating efficiency is improved.

For example, it is most preferable that the elastic members 800 be attached to the corners of the skin support member 700, respectively. Preferably, the assembly 140 having the conductive needles 100, the needle holding unit 200, and the electromagnetic wave transmitting unit 400 is preferably positioned at the height of the elastic members 800 attached to the skin support member 700. That is, the needle holding unit 200 is located in a region within 3 cm from the bottom of the skin support member 700.

Such a construction allows the conductive needles 100 inserted into the skin to be immediately removed therefrom within 2 seconds by the elasticity of the elastic members 800, and allows the needles 100 to be again rapidly inserted into the skin by being struck.

Meanwhile, an elastic structure may be provided instead of the elastic members 800 on the drive unit 300 so that the assembly 140 is moved up by the elasticity. That is, the elastic members 800, which differ in construction from the above-mentioned elastic members 800 and have elastic restoring force to move the needle holding unit 200 away from the skin, may accomplish the object of the invention. For example, the elastic members 800 may be placed between the needle holding unit 200 and the internal casing 600. The elastic members 800 may adopt various shapes, including those of a compression coil spring, a tension coil spring, and elastic rubber.

The assembly 140 may further include a memory unit 900 which contains data about the plurality of needles 100.

The memory unit 900 includes counting data about the number of times the needles 100 are inserted into the skin, time data about a time they are used after a mounting operation is first performed, and data about the arrangement and length of the conductive needles.

Further, a first connecting signal generated when the memory unit 900 is connected to a central processing unit (CPU) 1100 is transmitted to the CPU 1100 as time data. Thereafter, the CPU 1100 performs a counting operation for a preset time, and stops the operation of the assembly 140 after the preset time has passed. Further, the CPU 1100 counts the number of times the needles 100 are inserted into the skin, thus checking the lifespan of the needles 100.

When the needles 100 have been used for a lengthy period of time, the needles 100 become burnt or bent. Hence, after a predetermined amount of time has passed or they have been used for a preset number times, the CPU 1100 limits the use of the needles 100.

The electromagnetic waves preferably range from 10 KHz to 100 MHz. Since a pulsation period stimulating normal muscle of the body tissue ranges from 0.001 ms to 1 ms, that is, is very short, the application of the electromagnetic waves of high frequency is effective.

Preferably, the needle holding unit 200 is located within a distance of from 5 mm to 3 cm from the skin into which the needles 100 are to be inserted. If the needle holding unit 200 holding the plurality of needles 10 directly strikes the skin, pain is caused. When the distance between the needle holding unit 200 and the skin is less than 5 mm, pain which is the same as the pain when the needle holding unit 200 directly strikes the skin is caused. Meanwhile, if the distance between the needle holding unit 200 and the skin is greater than 3 cm, the needles 100 become long and thus may be easily bent.

Preferably, a first cover 620 which covers the internal casing 600 and a second cover 720 which covers the skin support member 700 and has a third hole 721 to transmit a force to the assembly 140 are further provided.

Hereinbefore, the plurality of needles 100 and peripheral components have been described. Now, the drive unit 300 will be described in detail.

The drive unit 300 directly or indirectly transmits a force to the needle holding unit 200 such that the needles 100 held by the needle holding unit 200 are inserted into the skin.

For example, in the case of directly transmitting the force, the drive unit 300 is directly secured to the needle holding unit 200 and performs a vertical motion so that the needles 100 are inserted into the skin. In contrast, in the case of indirectly transmitting the force, the drive unit 300 strikes the needle holding unit 200 and applies a force to the needle holding unit 200 to move it downward.

Figure 30:
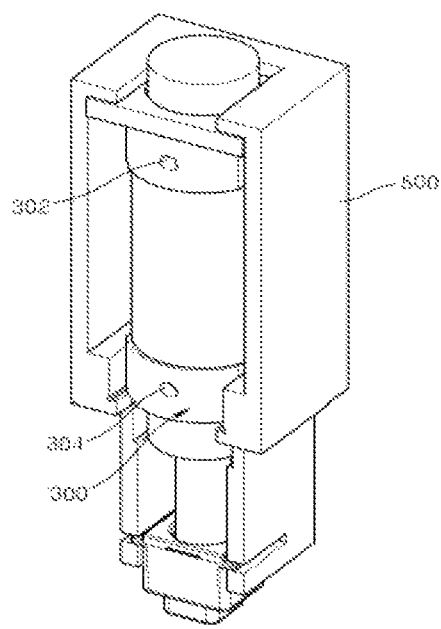
FIGS. 30 to 32 are views illustrating embodiments of the drive unit according to an embodiment of the invention.
Figure 31:
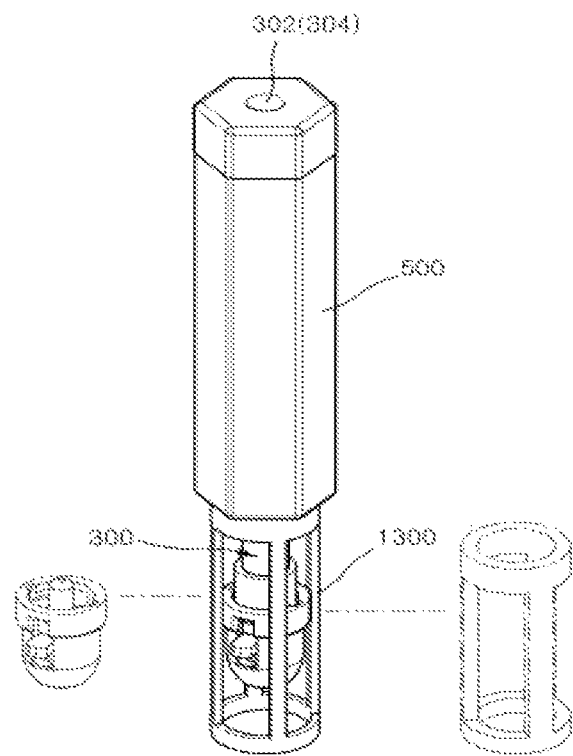
Figure 32:
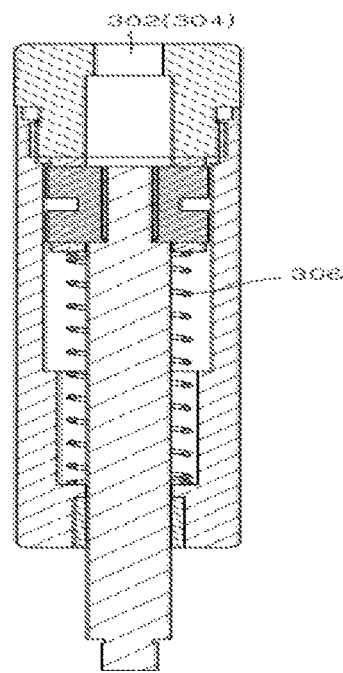

Preferably, the drive unit 300 is driven by any one of an electromagnetic valve, a hydraulic valve, a pneumatic valve, and a solenoid valve, which are operated by electric signals. FIGS. 30 and 31 illustrate the embodiments of the drive unit 300 which is driven by pneumatic force. The drive unit 300 of FIG. 30 is used in case the number of needles 100 is large. For example, referring to FIG. 30, the drive unit 300 driven by pneumatic force includes a pneumatic inlet 302 and a pneumatic outlet 304. The drive unit 300 is operated such that a rod moves downward when air flows from the pneumatic inlet 302 to the pneumatic outlet 304. Meanwhile, the drive unit 300 of FIG. 31 is used in case the number of needles 100 is small. The drive unit 300 of FIG. 31 uses the same port, as the pneumatic inlet 302 and the pneumatic outlet 304. That is, if air flows into the pneumatic inlet 302, the rod moves downward. Meanwhile, the upward movement of the rod is realized by a return spring 306. When the rod is moved upward by the elastic restoring force of the return spring 306, air introduced into the pneumatic inlet 302 is discharged from the pneumatic outlet 304.

Meanwhile, the drive unit 300 includes a first coupling part to allow the needle holding unit 200 to be fitted into and assembled with the first coupling part. Preferably, the drive unit 300 also includes a second coupling part 312 to allow an adjusting member 320, which is for adjusting the depth of the needles 100 inserted into the skin, to be assembled therewith.

Further, both the first coupling part for assembling the needle holding unit 200 and the second coupling part 312 for assembling the adjusting member 320 which is for adjusting the depth of the needles 100 inserted into the skin may be integrally formed on the drive unit 300.

Figure 18:
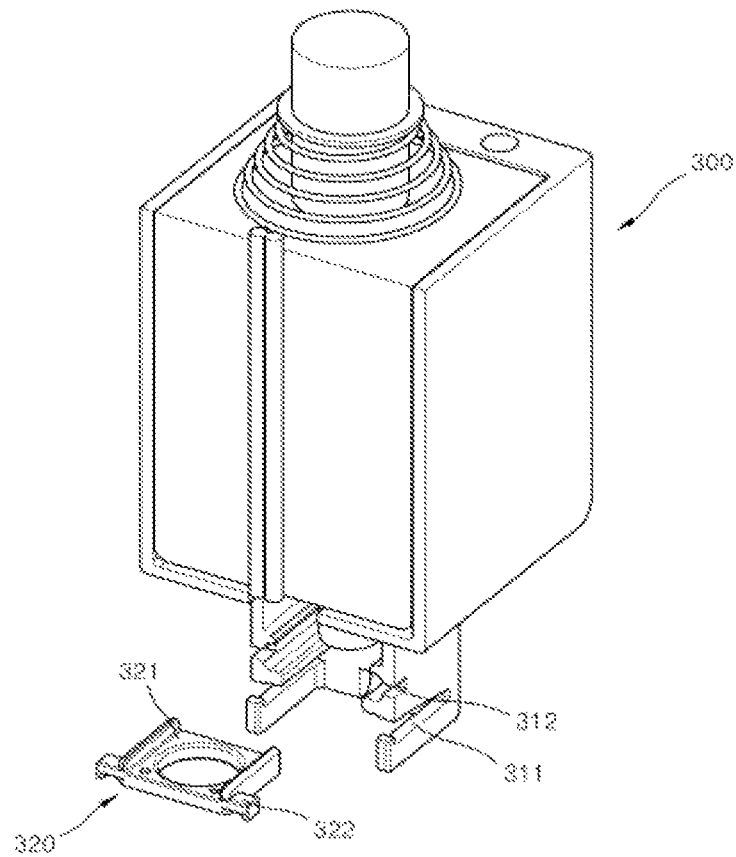
FIG. 18 is a view illustrating a drive unit according to an embodiment of the invention.

For example, as shown in FIG. 18, the first coupling part for assembling the needle holding unit 200 comprises first grooves 311, and the second coupling part for assembling the adjusting member 320 which adjusts the length of the needles inserted into the skin comprises second grooves 312.

In detail, as shown in FIG. 18, when the drive unit 300 is a solenoid valve, the first coupling part and the second coupling part may be integrated with the drive unit 300 and apply a force to the needles 100 so that they are inserted into the skin. The first and second coupling parts may be designed to be different from the structure of FIG. 18.

As shown in FIG. 18, the adjusting member 320 has on its opposite sides protrusions 322 which are fitted into the second grooves 312. The adjusting member 320 includes a body 321 which is integrated with the protrusions 322. The body 321 is fitted to the drive unit 300.

Figure 19:
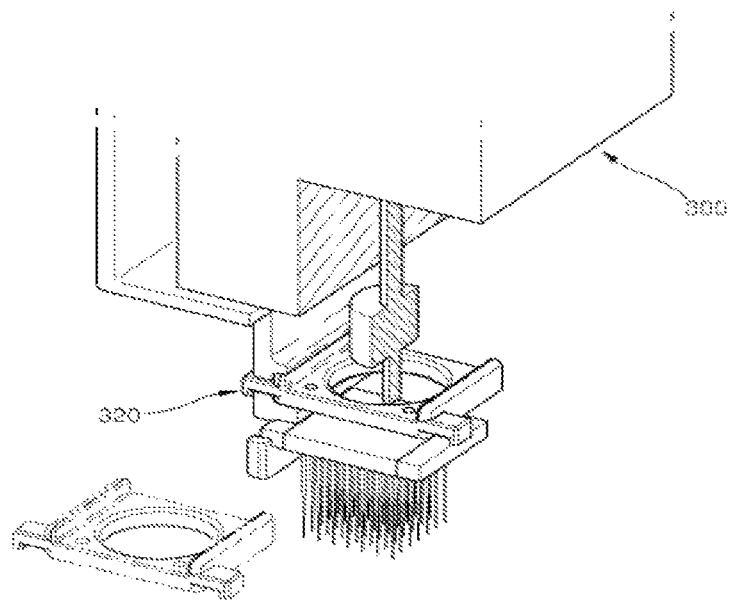
FIG. 19 is a view illustrating the operation of an adjusting member according to an embodiment of the invention.

For example, in the case of the solenoid valve as shown in FIG. 19, when the needles 100 are struck by a force of the drive unit 300, the height from which the striking takes place is determined by the thickness of the body 321. That is, if the body 321 is thin, the striking operation is performed at a higher position. In contrast, if the body 321 is thick, the striking operation is performed at a lower position. In this way, the depth of the needles 100 inserted into the skin is adjusted.

Consequently, the contact of the adjusting member with the drive unit when the body 321 is thick is performed prior to the contact when the body 321 is thin, so that force transmitted to the needles 100 is weak. Thus, the adjusting member 320 can adjust the depth of the needles 100 inserted into the skin.

Preferably, the adjusting member 320 may have a plurality of locking steps 330 at different heights to reduce a force transmitted to the needle holding unit 200, thus rotating in order to adjust the locking steps 330.

Figure 20:
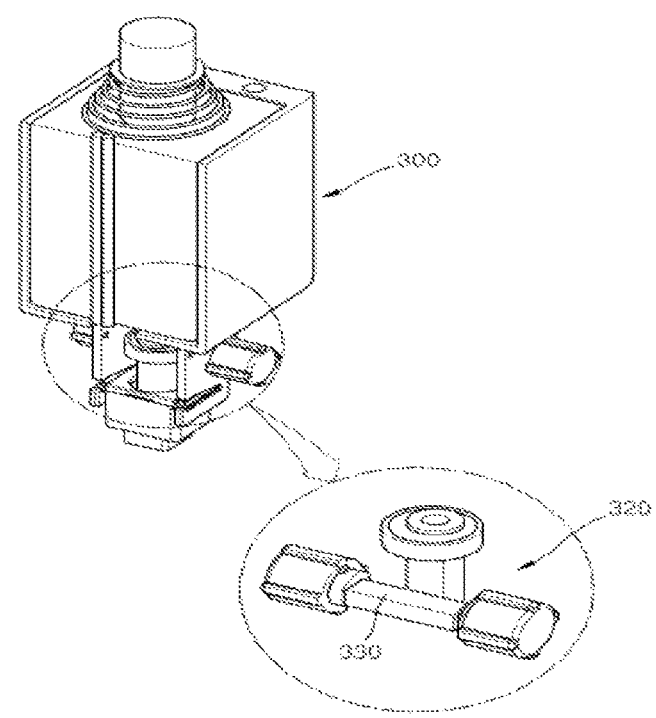
FIG. 20 is a view illustrating the use of another adjusting member according to an embodiment of the invention.

That is, the second grooves 312 may be modified to rotate the plurality of locking steps 330, thus controlling the intensity of force transmitted to the needles 100. As shown in FIG. 20, as the locking steps 330 rotate, the heights of the locking steps 330 change. The intensity of force generated by the drive unit 300 is adjusted by rotating the locking steps 330, and then the force is transmitted to the needles 100.

Figure 21:
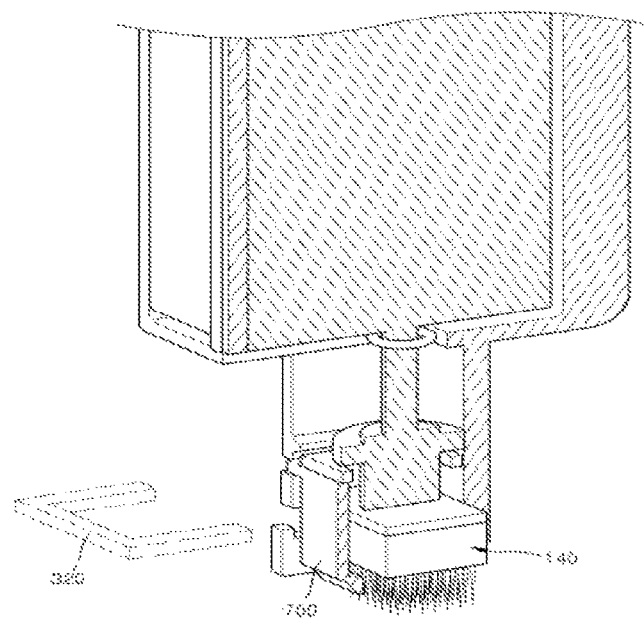
FIG. 21 is a view illustrating the use of a further adjusting member according to an embodiment of the invention.

Moreover, as shown in FIG. 21, a 'U'-shaped adjusting member is inserted into the first coupling part, and the skin support member 700 into which the assembly 140 is inserted is fitted into and assembled with the second coupling part. When the assembling operation is conducted in this way, force is transmitted to the assembly 140 by the drive unit 300, and the assembly 140 is moved downward by the transmitted force. Here, since the assembly 140 includes the needles 100, the needles 100 are inserted into the skin by the downward movement of the assembly 140.

When the assembly 140 provided in the skin support member 700 moves downward and the 'U'-shaped adjusting member is fitted into the second coupling part, the 'U'-shaped adjusting member is stopped by the internal casing within a range wherein the needles are not caught, thus controlling the forward moving force of the drive unit 300.

Figure 22:
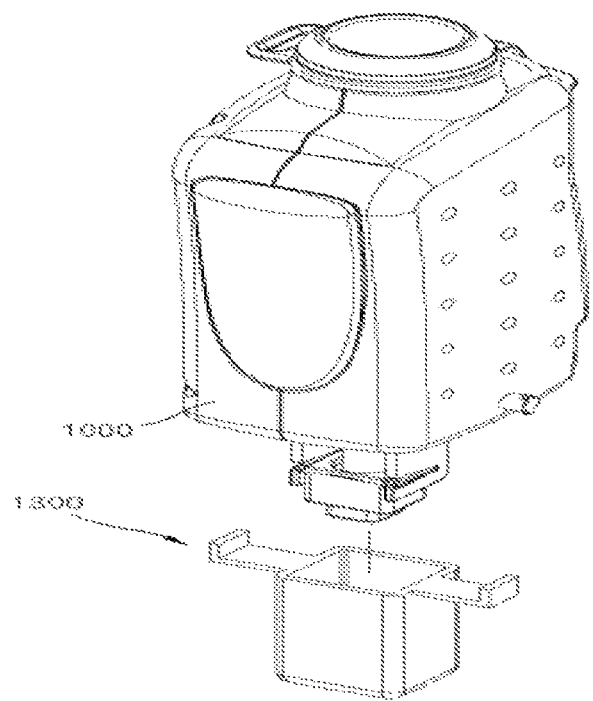
FIGS. 22 to 24 are views illustrating the shape of insertion limiting members according to an embodiment of the invention.
Figure 23:
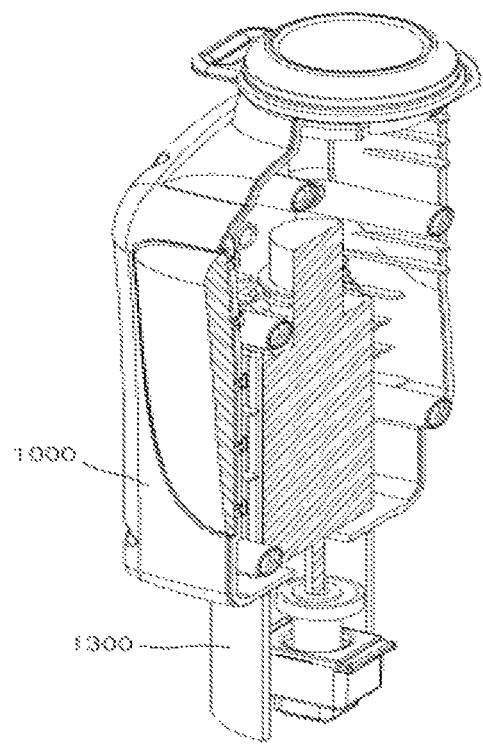
Figure 24:
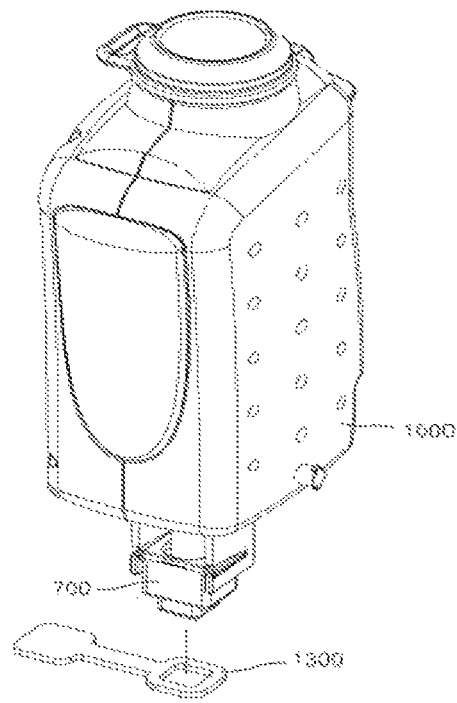
Figure 33:
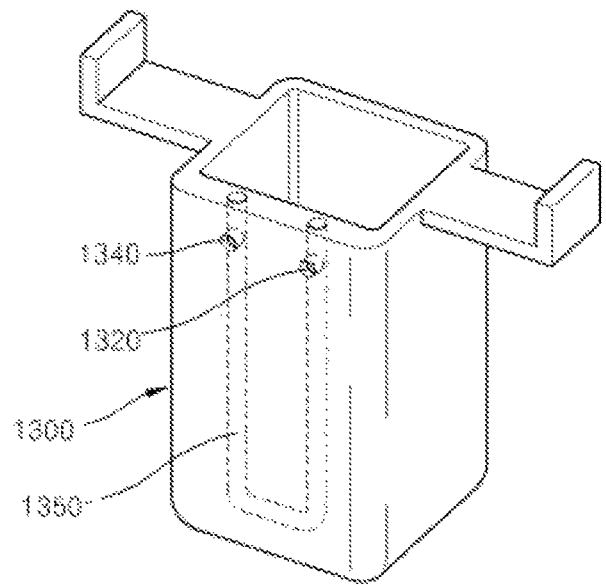
FIGS. 33 and 34 are views illustrating cooling structures for the insertion limiting member according to an embodiment of the invention.
Figure 34:
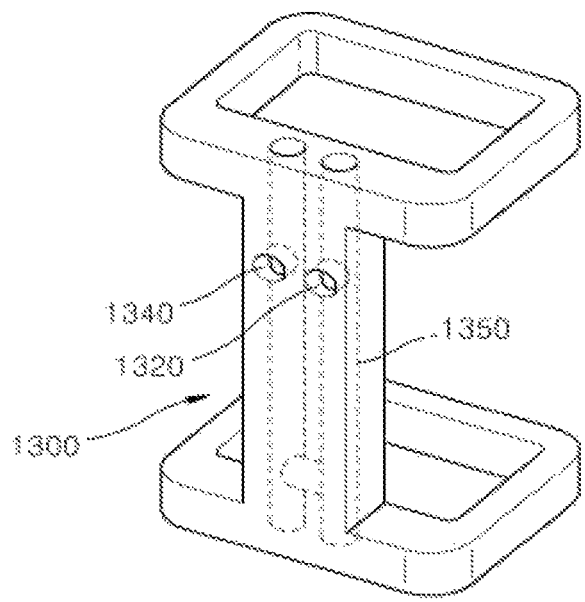

In a related context, a component substituting for the adjusting member 320 or an insertion limiting member 1300 cooperating with the adjusting member 320 may be further provided. The insertion limiting member 1300 functions to adjust the depth to which the needles 100 are inserted into the skin. One side of the insertion limiting member 1300 may be supported by the skin, while the other side may be supported by a casing 1000 as shown in FIG. 22 or 23. Meanwhile, one side of the insertion limiting member 1300 may be supported by the skin, while the other side may be supported by the skin support member 700 as shown in FIG. 24. The replacement of the insertion limiting member 1300 is possible. FIG. 31 shows another type of insertion limiting member 1300. Meanwhile, referring to FIGS. 33 and 34, the insertion limiting member 1300 may be provided with a cooling medium passage 1350 through which a cooling medium flows. The cooling medium passage 1350 is provided with a cooling medium inlet 1320 into which the cooling medium is introduced, and with a cooling medium outlet 1340. Various media including water or air may be used as the cooling medium. After the cooling medium fed into the cooling medium inlet 1320 flows through the cooling medium passage 1350, the cooling medium is discharged through the cooling medium outlet 1340. The cooling medium serves to cool the insertion limiting member 1300, thus alleviating the pain of a patient. Holes besides the cooling medium inlet 1320 or the cooling medium outlet 1340 of the cooling medium passage 1350 may be appropriately closed by stoppers.

After the electromagnetic wave transmitting unit 400 receives electromagnetic waves from the exterior through a cable, the electromagnetic wave transmitting unit 400 transmits the electromagnetic waves to the needles 100.

Meanwhile, the skin treating device 10 according to an embodiment of the invention may further include a cavity body 500. That is, the skin treating device 10 may include the plurality of needles 100, the needle holding unit 200, the drive unit 300, the electromagnetic wave transmitting unit 400, and the cavity body 500.

Since the needles 100, the needle holding unit 200, the drive unit 300, and the electromagnetic wave transmitting unit 400 are the same as those of the above-mentioned embodiment, the detailed description thereof will be omitted, and only the cavity body 500 will be described.

The cavity body 500 includes a third coupling part to allow the needle holding unit 200 to be fitted into and assembled with the third coupling part, and a fourth coupling part to allow the adjusting member 320, which is for adjusting the depth of the needles 100 inserted into the skin, to be assembled therewith. The third and fourth coupling parts have the same function as the first and second coupling parts.

For example, as shown in FIG. 25B, the cavity body 500 is provided with third grooves 531 and fourth grooves 532. The needle holding unit 200 is fitted into the third grooves 531. The third grooves 531 correspond to the first grooves 311. The adjusting member 320 for adjusting the depth of the needles 100 inserted into the skin is inserted into the fourth grooves 532. The fourth grooves 532 correspond to the second grooves 312. The third and fourth grooves 531 and 532 are integrally formed in the cavity body 500. The third and fourth grooves 531 and 532 may be formed separately from the cavity body 500 and then be assembled with the cavity body 500. A force is exerted on the needle holding unit 200 assembled with the cavity body 500 so that the needles 100 are inserted into the skin. The third and fourth coupling parts may be designed to have construction different from that of FIG. 25B.

The cavity body 500 is open at one side thereof so that the drive unit 300 is fitted therein. A water circulating structure is provided on a side surface of the cavity body 500 which is in contact with the drive unit 300, thus cooling heat generated from the drive unit 300.

Figure 25A:
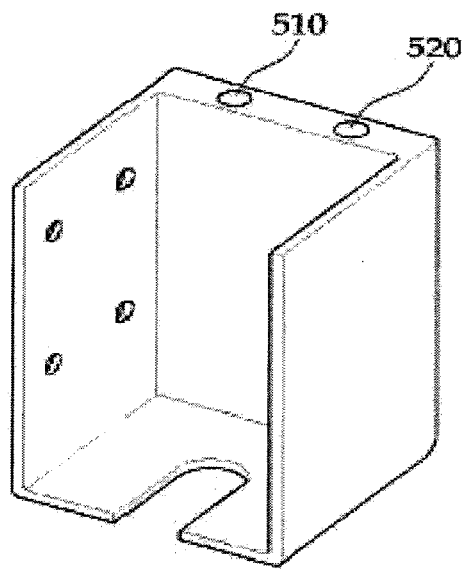
FIGS. 25A and 25B are views illustrating the construction of a cavity body according to an embodiment of the invention.
Figure 25:
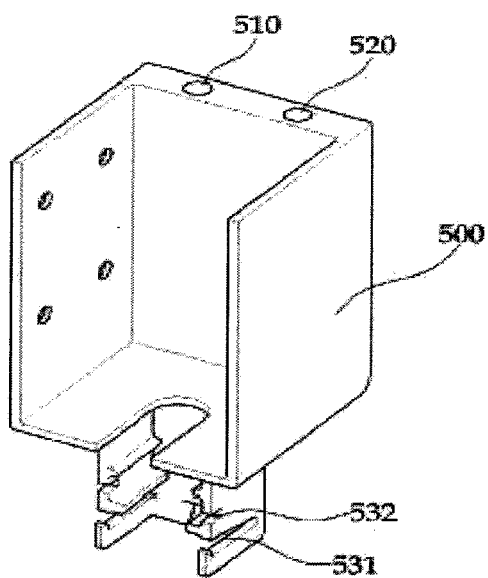
Figure 26:
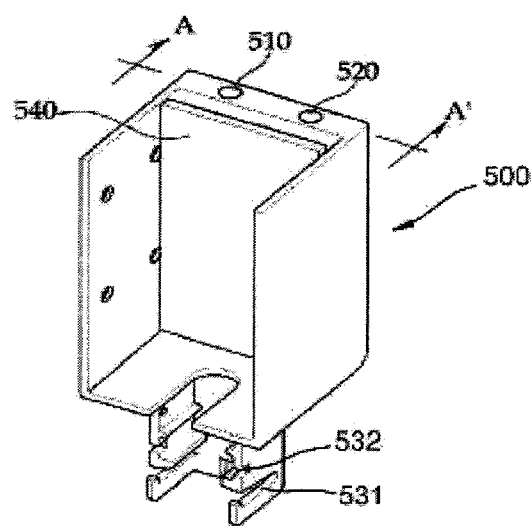
FIGS. 26A and 26B are views illustrating a cooling structure for a cavity body according to an embodiment of the invention.
Figure 26:
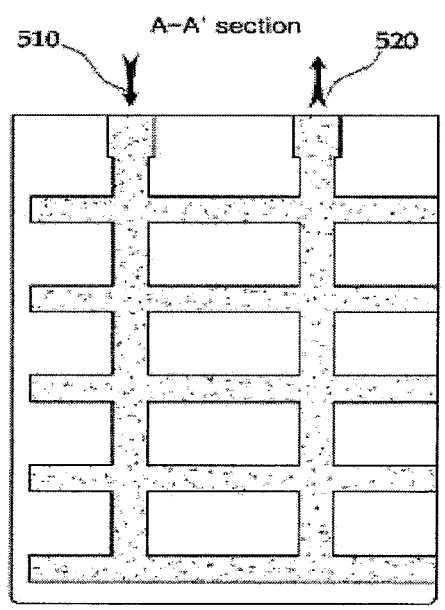

For example, as shown in FIGS. 25A and 25B, one side of the cavity body 500 is open so that the drive unit 300 is fitted and inserted therein. Referring to FIG. 26B that is the sectional view taken along line A-A' of FIG. 26A, the water circulating structure is provided on the side surface of the cavity body 500 which is in contact with the drive unit 300. The drive unit 300 includes an inlet 510 into which water is introduced, and an outlet 520 through which water is discharged. After water injected through the inlet 510 has circulated, the water is discharged through the outlet 520.

Figure 27:
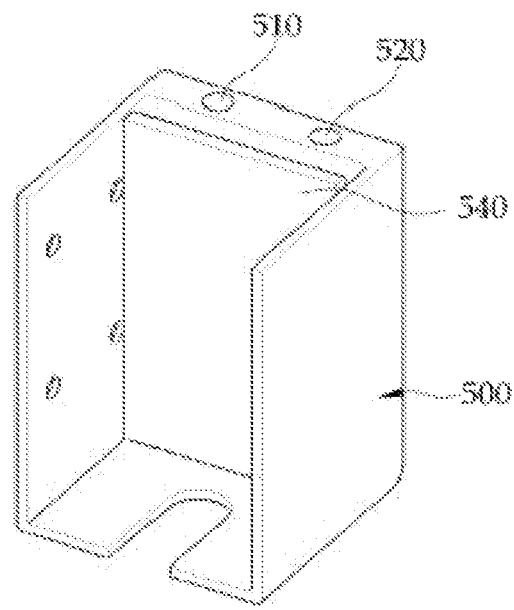
FIG. 27 is a view illustrating the construction of a thermoelement provided in the cavity body according to an embodiment of the invention.

Further, as shown in FIG. 27, the cavity body 500 is provided with a thermoelement 540. The thermoelement 540 functions to cool the drive unit 300 which emits heat. The thermoelement 540 is constructed so that a portion which is in contact with the drive unit 300 is maintained at a low temperature and a portion which is opposite to the drive-unit contact portion is maintained at a higher temperature. The thermoelement 540 is provided on a side surface of the cavity body 500 on which the inlet 510 and the outlet 520 are formed.

Moreover, an air cooling structure may be used to substitute for the water circulating structure. Preferably, the air cooling structure is formed such that external cold air is introduced into the inlet 510 and then is discharged through the outlet 520 to the outside.

Figure 28:
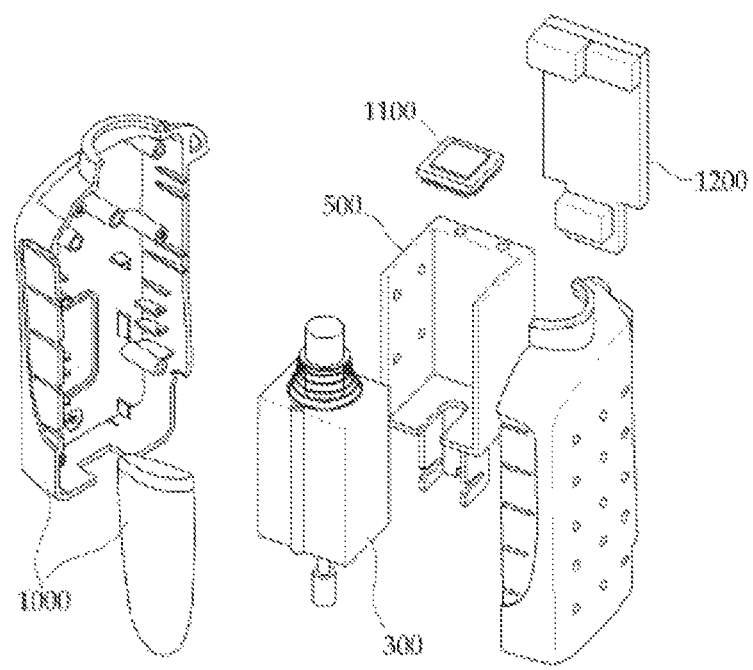
FIG. 28 is a view illustrating the assembly of the drive unit according to an embodiment of the invention.

Preferably, as shown in FIG. 28, the casing 1000 is further provided to protect the plurality of needles 100, the needle holding unit 200, the drive unit 300, the electromagnetic wave transmitting unit 400, and the cavity body 500.

Further, as shown in FIG. 28, the CPU 1100 is preferably provided to process all data for operating the skin treating device according to an embodiment of the invention. The data processed by the CPU 1100 includes data on the lifespan of the drive unit 300, data on the needles 100 (the number of needles and the length of needles), data on the electromagnetic wave voltage, and data on the time that the electromagnetic waves are output.

Especially, when the data on the needles 100 transmitted to the memory unit 900 is identical to the data on the needles 100 stored in the memory unit 900, the device works. In contrast, when the transmitted data is not identical with the stored data, the device does not work.

Moreover, the CPU 1100 performs control such that, when a characteristic number received from the memory unit 900 is different from an input characteristic number, the device does not work. If the received characteristic number is identical to the input characteristic number, a counting operation is performed to reach a preset time corresponding to the lifespan. After the preset time has passed, the operation of the assembly 140 is stopped.

Further, the CPU 1100 checks the lifespan of the needles 100 by counting the number of times the needles 100 have been inserted into the skin. Preferably, the CPU 1100 may check the lifespan of the needles 100 by counting the number of times the drive unit 300 transmits force to the needles 100. The CPU 1100 may perform a counting operation by detecting the movement of the needles 100 using a sensor. As such, the CPU 1100 may check the lifespan of the needles 100 in various methods. The reason why the CPU 1100 checks the lifespan of the needles 100 is because the needles 100 which are bent, broken or worn out at ends thereof must be replaced with new ones.

The memory unit 900 may be directly connected to the CPU 1100. However, a connector 1200 may be further provided to allow the memory unit 900 to be smoothly replaced by another one.

Figure 29:
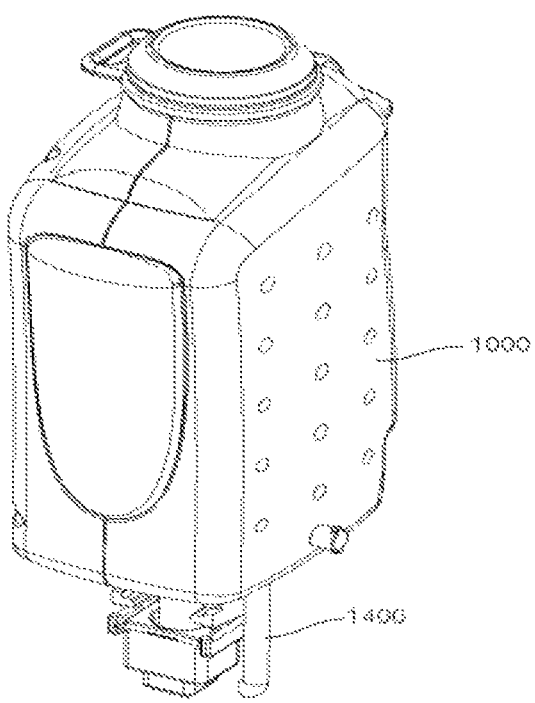
FIG. 29 is a view illustrating a cold air injection nozzle according to an embodiment of the invention.

In a related context, as shown in FIG. 29, the casing 1000 is provided with a cold air injection nozzle 1400. The cold air injection nozzle 1400 functions to cool skin which is to be treated, before or after the needles 100 have been inserted. The cold air injection nozzle 1400 sprays cold air, fed from the outside of the casing 1000 to a cold air inflow passage (not shown), onto the skin under regular pressure. The cold air injection nozzle 1400 protrudes from the casing 1000 toward the skin. The cold air sprayed from the cold air injection nozzle 1400 cools the skin, thus removing the pain and aiding in healing a wound.

Figure 35:
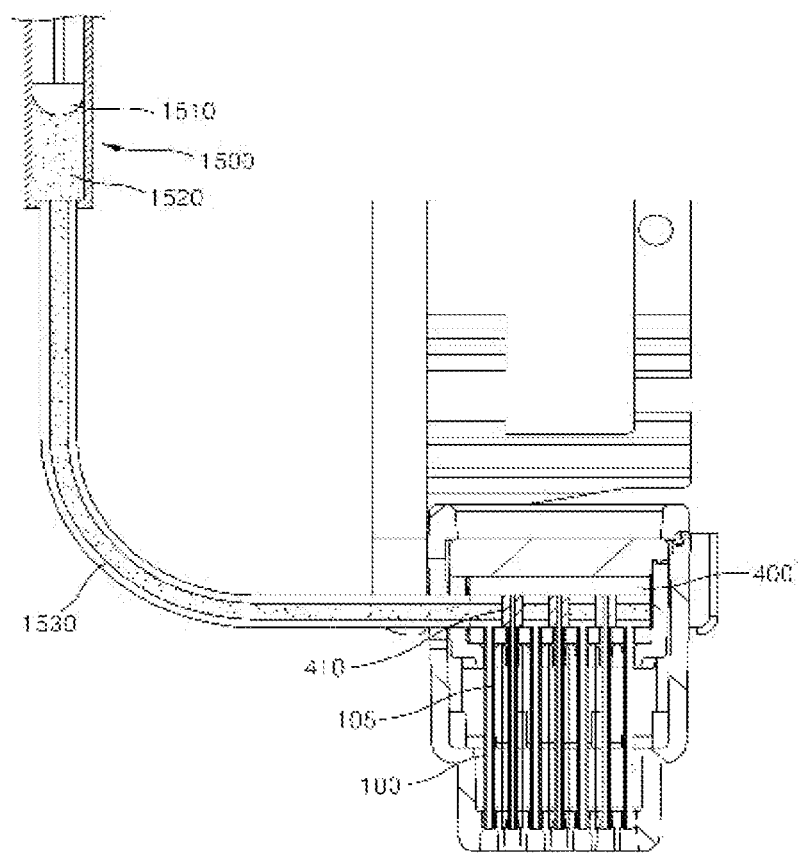
FIG. 35 is a view illustrating a drug feeding structure according to an embodiment of the invention.

Referring to FIG. 35, according to another embodiment of the invention, each needle 100 is provided with a drug feeding tube 105. The drug feeding tube 105 extends in the longitudinal direction of the needle 100 in such a way as to pass from the upper end to the lower end of the needle 100. In the state in which each needle 100 has been inserted into the skin, the drug feeding tube 105 feeds a required drug into the skin. One end of a drug supply passage 1530 is connected to the upper portions of the needles 100 to supply the drug to only some of the needles 100. Transmitting members 410 are connected to the upper portions of the remaining needles 100 to transmit electromagnetic waves from the electromagnetic wave transmitting unit 400 to the needles 100. That is, a drug is not supplied to the needles 100 equipped with the transmitting members 410. The other end of the drug supply passage 1530 is connected to a drug feeding unit 1500. The drug feeding unit 1500 is a kind of syringe pump and has a piston 1510 which is compressed. The drug feeding unit 1500 contains a drug 1520 therein. The piston 1510 may be constructed to be subjected to a pressure by a power means, for example, a motor, pneumatic means, or hydraulic means. The skin treating device constructed as shown in FIG. 35 injects the drug into one part of the skin and transmits the electromagnetic waves to the other part, with needles 100 being inserted into the skin, thus enabling the effective treatment of the skin.

Although the various embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A device for skin treatment of a patient's skin, comprising:
    a plurality of needles, a portion of each of the needles except for a sharp end being coated with an insulator;
    a needle holding unit for holding the needles;
    a drive unit for directly or indirectly transmitting a force to the needle holding unit, thus allowing the needles held by the needle holding unit to be inserted into the skin;
    an electromagnetic wave transmitting unit electrically connected to the needles and transmitting electromagnetic waves to the needles;
    an internal casing being open in an upper portion thereof such that the needles, the needle holding unit, and the electromagnetic wave transmitting unit are fitted therein to be protected, and having in a lower portion thereof a plurality of first holes to permit passage of the needles;
    a first cover for covering the internal casing;
    a skin support member being open in an upper portion thereof such that an assembly having the needles, the needle holding unit, the electromagnetic wave transmitting unit and the internal casing is inserted into the open upper portion, and having in a lower portion thereof arranged for contacting the skin a plurality of second holes such that the needles pass through the second holes;
    a second cover for covering the skin support member;
    an elastic member having an elastic restoring force to move the needle holding unit away from the skin;
    wherein the elastic member is placed between the needle holding unit and the first holes or between the needle holding unit and the second holes;
    a memory unit having data on the plurality of needles;
    wherein the drive unit comprises an adjusting member to adjust an insertion depth of the needles into the skin, the adjusting member comprising bodies of different thicknesses to directly or indirectly control forward movement of the drive unit, so that a body of the adjusting member is fitted into the drive unit.

2. The device as set forth in claim 1, wherein the drive unit comprises a first coupling part such that the needle holding unit is fitted therein.

3. The device as set forth in claim 2, wherein the drive unit comprises a second coupling part which is provided separately from the first coupling part to allow the adjusting member to be coupled to the second coupling part, the drive unit being stopped by the adjusting member to directly or indirectly control forward movement of the drive unit.

4. The device as set forth in claim 1, wherein the adjusting member comprises a plurality of locking steps of different thicknesses, and directly or indirectly controls forward movement of the drive unit by rotating the locking steps.

5. The device as set forth in claim 1, wherein the drive unit comprises one selected out from a group consisting of an electromagnetic valve, a hydraulic valve, a pneumatic valve, and a solenoid valve, which are operated by electric signals.

6. The device as set forth in claim 1, wherein the electromagnetic wave transmitting unit receives electromagnetic waves from an outside through a cable, and thereafter transmits the electromagnetic wave to the plurality of needles.

7. The device as set forth in claim 1, further comprising:
    a central processing unit (CPU) configured to receive a characteristic number of the needles, recorded and stored in the memory unit, from the memory unit, to compare the received characteristic number with an input characteristic number, and to stop operation of the needles when the received characteristic number is identical with the input characteristic number.

8. The device as set forth in claim 1, wherein the skin support member is made of a stainless steel or aluminum material.

9. The device as set forth in claim 1, wherein a first end of each of the needles has a diameter ranging from 0.1 mm to 0.4 mm.

10. The device as set forth in claim 1, wherein each of the needles is bent in at least one stage such that an angle thereof is changed between a first end and the sharp second end of the needle.

11. The device as set forth in claim 1, wherein each of the needles is rounded without being bent between a first end and the sharp second end of the needle.

12. The device as set forth in claim 1, wherein the portion of each of the needles except for the sharp end is coated with any one of Parylene, Teflon, and ceramic to a thickness of 5 μm to 25 μm.

13. The device as set forth in claim 1, wherein each of the needles is shaped such that a first straight line connecting a first point which is in contact with the skin when the needle is inserted into the skin with a sharp point of the sharp end forms an angle of 14° to 30° with a second straight line connecting a second point which faces the first point with the sharp point of the sharp end.

14. The device as set forth in claim 1, wherein an interval between neighboring needles ranges from 0.4 mm to 3.0 mm.

15. The device as set forth in claim 1, wherein an insertion depth of the needles into the skin ranges from 0.3 mm to 2.5 cm.

16. The device as set forth in claim 1, wherein a distance from a first needle to a last needle placed on an end facing the first needle ranges from 2 mm to 20 mm.

17. The device as set forth in claim 1, wherein the plurality of needles comprises 4 to 81 needles.

18. The device as set forth in claim 1, wherein, immediately after the needles are inserted into the skin by being struck, the needles are removed from the skin within 2 seconds using elasticity of the elastic member.

19. The device as set forth in claim 1, wherein the electromagnetic waves range from 10 KHz to 100 MHz.

20. The device as set forth in claim 1, wherein the needle holding unit is positioned at a distance of 5 mm to 3 cm from the skin into which the needles are to be inserted.

21. The device as set forth in claim 1, wherein
each of the needles comprises a drug feeding tube which passes through the needle in a longitudinal direction thereof,
a first end of a drug supply passage is connected to upper portions of the needles to supply a drug to only some of the needles, and a transmitting member is provided on the remaining needles to transmit electromagnetic waves from the electromagnetic wave transmitting unit to the associated needles, and
a drug feeding unit is connected to a second end of the drug supply passage, contains a drug, and is compressed by a piston.

22. The device as set forth in claim 1, wherein the drive unit is not connected to the needle holding unit and as a result is spaced apart therefrom by a predetermined distance, and is driven in response to electric signals, thus striking the needle holding unit.

23. A device for skin treatment of a patient's skin, comprising:
a plurality of needles, a portion of each of the needles except for a sharp end being coated with an insulator;
a needle holding unit for holding the needles;
a drive unit for directly or indirectly transmitting a force to the needle holding unit, thus allowing the needles held by the needle holding unit to be inserted into the skin;
an electromagnetic wave transmitting unit electrically connected to the needles and transmitting electromagnetic waves to the needles;
an internal casing being open in an upper portion thereof such that the needles, the needle holding unit, and the electromagnetic wave transmitting unit are fitted therein to be protected, and having in a lower portion thereof a plurality of first holes to permit passage of the needles;
a first cover for covering the internal casing;
a skin support member being open in an upper portion thereof such that an assembly having the needles, the needle holding unit, the electromagnetic wave transmitting unit and the internal casing is inserted into the open upper portion, and having in a lower portion thereof arranged for contacting the skin a plurality of second holes such that the needles pass through the second holes;
a second cover for covering the skin support member;
an elastic member having an elastic restoring force to move the needle holding unit away from the skin;
wherein the elastic member is placed between the needle holding unit and the first holes or between the needle holding unit and the second holes;
a memory unit having data on the plurality of needles;
a cavity body being open at a first side surface thereof such that the drive unit is inserted therein, and being partially open at a lower portion thereof such that the drive unit applies a force to the needle holding unit; and
an adjusting member to adjust an insertion depth of the needles into the skin, the adjusting member comprising bodies of different thicknesses to directly or indirectly control forward movement of the drive unit.

24. The device as set forth in claim 23, wherein the cavity body comprises on a surface contacting the drive unit a water circulating structure to cool heat generated from the drive unit.

25. The device as set forth in claim 23, wherein the cavity body further comprises a thermoelement, a portion of the thermoelement which is in contact with the drive unit being lower in temperature than the drive unit, and a portion of the thermoelement which is opposite to the drive unit contact portion being higher in temperature than the drive unit contact portion.

26. The device as set forth in claim 23, wherein the cavity body comprises a first coupling part into which the needle holding unit is fitted.

27. The device as set forth in claim 26, wherein the cavity body comprises a second coupling part which is provided separately from the first coupling part to allow the adjusting member to be coupled to the second coupling part, the drive unit being stopped by the adjusting member to directly or indirectly control forward movement of the drive unit.

28. The device as set forth in claim 2, wherein the skin support member is made of a stainless steel or aluminum material.

29. The device as set forth in claim 23, further comprising an outer casing, wherein the outer casing comprises a cold air injection nozzle which protrudes toward the skin and sprays cold air, fed from an outside, onto the skin.

30. A device for skin treatment of a patient's skin, comprising:
a plurality of needles, a portion of each of the needles except for a sharp end being coated with an insulator;

a needle holding unit for holding the needles;

a drive unit for directly or indirectly transmitting a force to the needle holding unit, thus allowing the needles held by the needle holding unit to be inserted into the skin; and an electromagnetic wave transmitting unit electrically connected to the needles and transmitting electromagnetic waves to the needles;

an internal casing being open in an upper portion thereof such that the needles, the needle holding unit, and the electromagnetic wave transmitting unit are fitted therein to be protected, and having in a lower portion thereof a plurality of first holes to permit passage of the needles;

a first cover for covering the internal casing;

a skin support member being open in an upper portion thereof such that an assembly having the needles, the needle holding unit, the electromagnetic wave transmitting unit and the internal casing is inserted into the open upper portion, and having in a lower portion thereof arranged for contacting the skin a plurality of second holes such that the needles pass through the second holes;

a second cover for covering the skin support member;

an elastic member having an elastic restoring force to move the needle holding unit away from the skin;

wherein the elastic member is placed between the needle holding unit and the first holes or between the needle holding unit and the second holes;

a memory unit having data on the plurality of needles; and an adjusting member to adjust an insertion depth of the needles into the skin, the adjusting member comprising bodies of different thicknesses to directly or indirectly control forward movement of the drive unit;

wherein the needles held by the needle holding unit have two or more kinds of lengths.

31. A device for skin treatment of a patient's skin, comprising:

a plurality of needles, a portion of each of the needles except for a sharp end being coated with an insulator;

a needle holding unit for holding the needles;

a drive unit for directly or indirectly transmitting a force to the needle holding unit, thus allowing the needles held by the needle holding unit to be inserted into the skin;

an electromagnetic wave transmitting unit electrically connected to the needles and transmitting electromagnetic waves to the needles;

an insertion limiting member arranged to be supported at a side thereof by the skin to adjust an insertion depth to which the needles are inserted into the skin, the insertion limiting member being replaceable by another insertion limiting member;

an internal casing being open in an upper portion thereof such that the needles, the needle holding unit, and the electromagnetic wave transmitting unit are fitted therein to be protected, and having in a lower portion thereof a plurality of first holes to permit passage of the needles;

a first cover for covering the internal casing;

a skin support member being open in an upper portion thereof such that an assembly having the needles, the needle holding unit, the electromagnetic wave transmitting unit and the internal casing is inserted into the open upper portion, and having in a lower portion thereof arranged for contacting the skin a plurality of second holes such that the needles pass through the second holes;

a second cover for covering the skin support member;

an elastic member having an elastic restoring force to move the needle holding unit away from the skin; and an adjusting member to adjust an insertion depth of the needles into the skin, the adjusting member comprising bodies of different thicknesses to directly or indirectly control forward movement of the drive unit;

a memory unit having data on the plurality of needles;

wherein the elastic member is placed between the needle holding unit and the first holes or between the needle holding unit and the second holes.

32. The device as set forth in claim 31, wherein the insertion limiting member comprises:

a cooling medium passage through which a cooling medium circulates;

a cooling medium inlet provided in the cooling medium passage and permitting an inflow of the cooling medium; and a cooling medium outlet discharging the cooling medium which flows into the cooling medium inlet and has circulated in the cooling medium passage.

* * * * *